United States Patent
Kim et al.

(10) Patent No.: US 12,403,220 B2
(45) Date of Patent: Sep. 2, 2025

(54) SCAFFOLDS FOR CARTILAGE REGENERATION AND METHOD FOR TREATMENT OF CARTILAGE DEFECTS USING THE SAME

(71) Applicant: INDUSTRY FOUNDATION OF CHONNAM NATIONAL UNIVERSITY, Gwangju (KR)

(72) Inventors: Jangho Kim, Gwangju (KR); Jong Keun Seon, Gwangju (KR); Sunho Park, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 699 days.

(21) Appl. No.: 17/479,057

(22) Filed: Sep. 20, 2021

(65) Prior Publication Data
US 2023/0211049 A1    Jul. 6, 2023

(51) Int. Cl.
 *A61L 27/38*    (2006.01)
 *A61L 27/36*    (2006.01)

(52) U.S. Cl.
 CPC ......... *A61L 27/3834* (2013.01); *A61L 27/365* (2013.01); *A61L 27/3654* (2013.01); *A61L 2400/12* (2013.01); *A61L 2400/18* (2013.01); *A61L 2430/02* (2013.01); *A61L 2430/06* (2013.01)

(58) Field of Classification Search
 CPC .............. A61L 27/3834; A61L 27/365; A61L 27/3654; A61L 2400/12; A61L 2400/18; A61L 2430/02; A61L 2430/06
 See application file for complete search history.

(56) References Cited

U.S. PATENT DOCUMENTS

| | | | | |
|---|---|---|---|---|
| 2006/0085063 A1* | 4/2006 | Shastri | A61L 27/383 | 623/1.49 |
| 2007/0233272 A1* | 10/2007 | Boyce | A61L 27/3691 | 623/23.63 |
| 2007/0269481 A1* | 11/2007 | Li | A61P 17/02 | 425/174.8 E |
| 2008/0260694 A1* | 10/2008 | Gronthos | A61P 19/00 | 435/372 |
| 2009/0074832 A1* | 3/2009 | Zussman | A61L 27/3821 | 606/151 |
| 2010/0168746 A1* | 7/2010 | Griffey | A61F 2/30721 | 424/423 |
| 2010/0292791 A1* | 11/2010 | Lu | A61P 37/06 | 623/13.12 |
| 2010/0331980 A1* | 12/2010 | Lee | A61L 27/3826 | 623/14.13 |
| 2013/0197663 A1* | 8/2013 | MacEwan | A61F 2/0063 | 623/23.72 |
| 2013/0338791 A1* | 12/2013 | McCullen | A61L 27/38 | 623/23.72 |

(Continued)

*Primary Examiner* — Alvin J Stewart
(74) *Attorney, Agent, or Firm* — PLEECHAE IP, LLC

(57) ABSTRACT

A scaffold according to an embodiment of the present disclosure is for cartilage regeneration. The scaffold may include a plurality of linear nano-patterns aligned in one direction, and stem cells adhered to the plurality of linear nano-patterns. The scaffold May improve regeneration and maturity of the cartilage, thereby being effectively used in treatment of cartilage defects.

16 Claims, 7 Drawing Sheets
Specification includes a Sequence Listing.

(56) References Cited

U.S. PATENT DOCUMENTS

2016/0017268 A1* 1/2016 Kim ...................... C12M 41/46
                                                          435/287.1
2018/0280570 A1* 10/2018 Poundarik ......... A61F 13/00063
2021/0298908 A1* 9/2021 Holmes ............... A61F 2/30756

* cited by examiner

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
ttcagctatg gagatgacaa tc                                              22

<210> SEQ ID NO 2
<211> LENGTH: 22
<212> TYPE: DNA
<213> ORGANISM: Artificial Sequence
```

```
<220> FEATURE:
<223> OTHER INFORMATION: primer

<400> SEQUENCE: 2
ttcagctatg gagatgacaa tc                                              22

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gaaggtgaag gtcggagtca                                                 20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gaagatggtg atgggatttc                                                 20
```

SCAFFOLDS FOR CARTILAGE REGENERATION AND METHOD FOR TREATMENT OF CARTILAGE DEFECTS USING THE SAME

BACKGROUND

1. Technical Field

The present invention relates to a support ("scaffold") for cartilage regeneration and a method for treatment of cartilage defects using the same.

2. Background of the Invention

Articular cartilage ("cartilage") is a bone tissue consisting of chondrocytes and a cartilage matrix surrounding the same.

The chondrocyte functions to synthesize and secrete a cartilage matrix in the articular cartilage. The cartilage matrix endows elasticity to the cartilage. Unlike other tissues, the cartilage does not include blood vessels or nerves distributed therein, and therefore, if the cartilage is damaged once, it is difficult to regenerate the same. As such, due to the lack of self-repair capability, a surgery treatment such as microfracture techniques is required to treat cartilage defects.

The microfracture technique is a surgical operation to regenerate defected cartilage, and utilizes a principle in which microfine fractures are given on an exposed bone having defects, and when a subchondral bone is damaged, a marrow component including marrow stem cells may leak, which in turn occurs differentiation of these cells thus to form a cartilage.

However, most of such generated cartilages are formed as fibrous cartilage ("fibrocartilage") rather than hyaline cartilage. Such fibrocartilage is enriched with Type 1 collagen while having a low content of proteoglycan, hence causing a deterioration in tolerance to abrasion. Accordingly, if defected cartilage tissues are regenerated into fibrocartilages, symptoms may be improved by about 60 to 70% till about 2 years after surgery. However, thereafter, structural degradation may occur which in turn sometimes causes worse symptoms. Further, it is known that, the bigger the cartilage defect site, the more sever the symptom. A treatment method based on the microfracture technique alone has a limitation in treatment in regard to a wide range of cartilage defects, and entails a disadvantage of regenerating fibrocartilage having lower mechanical properties.

Therefore, as a result of studies and efforts to develop a cartilage treatment method that can promote cartilage regeneration and improve maturity during cartilage regeneration, the present inventors have found that cartilage defects may be effectively treated by attaching a scaffold of the present invention to the cartilage defect site, and therefore, the present invention has been completed on the basis of the above finding.

SUMMARY

An object of the present invention is to provide a scaffold effective to regenerate a cartilage.

In addition, another object of the present invention is to provide a treatment method of cartilage defects using the scaffold of the present invention.

1. A scaffold, including: a plurality of linear nano-patterns aligned in one direction; and stem cells adhered to the nano-patterns.
2. The scaffold according to the above 1, wherein the pattern includes a ridge and a groove having each independently a width of 100 to 1000 nm.
3. The scaffold according to the above 1, wherein the pattern has a height of 100 to 1000 nm.
4. The scaffold according to the above 1, wherein the stem cells are mesenchymal stem cells derived from human adipose tissues.
5. The scaffold according to the above 1, wherein the scaffold is used to be adhered to a microfracture site of a bond exposed due to cartilage defects.
6. A method for treatment of cartilage defects, including: adhering a scaffold, which comprises a plurality of linear nano-patterns aligned in one direction, to a cartilage defect site so that a surface having the nano-patterns formed thereon comes into contact with the cartilage defect site of a subject.
7. The method according to the above 6, further including: adhering stem cells to the nano-patterns before adhesion of the scaffold.
8. The method according to the above 6 or 7, wherein the pattern includes a ridge and a groove having each independently a width of 100 to 1000 nm.
9. The method according to the above 6 or 7, wherein the pattern has a height of 100 to 1000 nm.
10. The method according to the above 7, wherein the stem cells are mesenchymal stem cells derived from human adipose tissues.
11. The method according to the above 6 or 7, further including: microfracture of a bone exposed on the cartilage defect site, wherein the scaffold is adhered to the microfractured site.

The present invention may provide a scaffold for cartilage treatment and a treatment method of cartilage defects using the scaffold described above. Herein, the scaffold of the present invention may include a plurality of linear nano-patterns aligned in one direction, and may enhance regeneration of cartilages and maturity, thereby being effectively used in treatment of cartilage defects.

Figure 1:
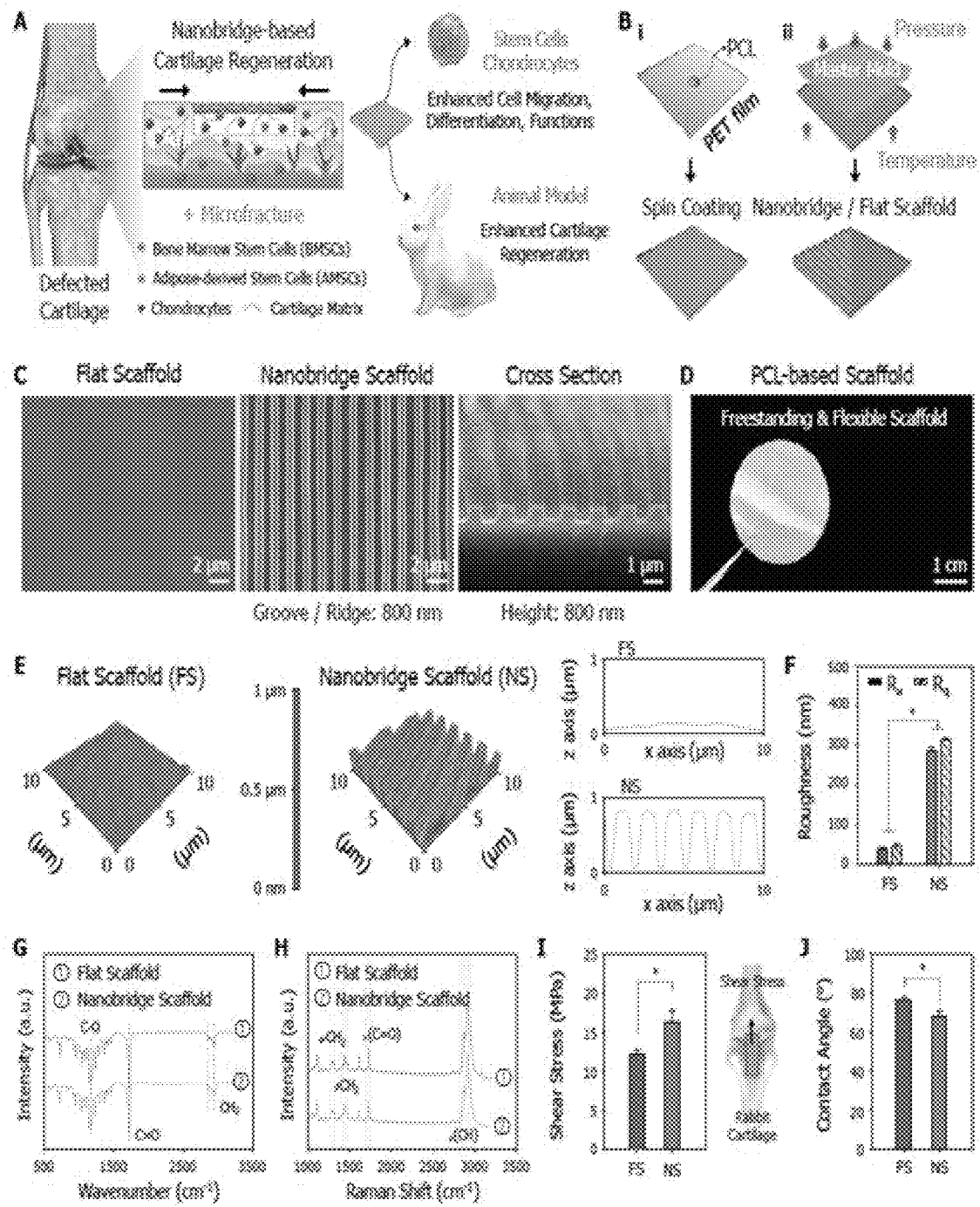
FIG. 1 illustrates rational design for the development of the nanobridge scaffold for cartilage regeneration.

A of FIG. 1 illustrates schematic of the synergistic effects of the stem cells and nanobridge scaffold for cartilage regeneration.

B of FIG. 1 illustrates schematic of the scaffold fabrication process using the nanobioimprinting technique.

C of FIG. 1 illustrates scanning electron microscopy images of the fabricated flat and nanobridge scaffolds.

D of FIG. 1 illustrates representative photograph of the freestanding and flexible nanobridge scaffold.

E of FIG. 1 illustrates atomic force micrographs of the flat and nanobridge scaffolds.

F of FIG. 1 illustrates roughness of the flat and nanobridge scaffolds.

G of FIG. 1 illustrates FTIR spectra of the flat and nanobridge scaffolds.

H of FIG. 1 illustrates Raman spectra of the flat and nanobridge scaffolds.

I of FIG. 1 illustrates shear stress of the flat and nanobridge scaffolds on rabbit cartilage tissue.

J of FIG. 1 illustrates water contact angles of the flat and nanobridge scaffolds.

Error bars represent the standard deviation about the means (n=5 for each group). Data were analyzed by one-way ANOVA (*P<0.05).

Figure 2:
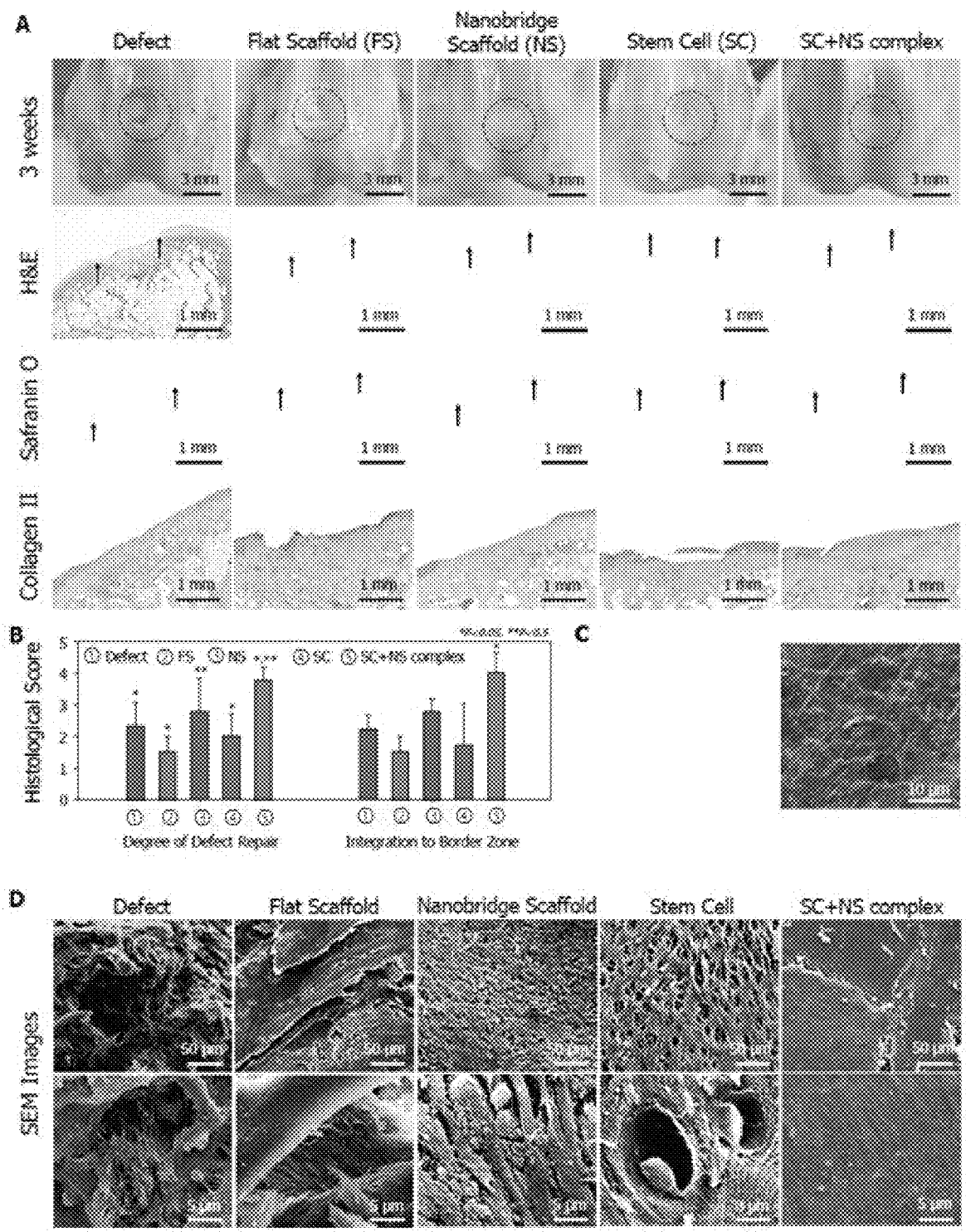

FIG. 2 illustrates effects of the transplantable stem cells nanobridge scaffold on cartilage regeneration.

A of FIG. 2 illustrates macroscopic appearances, and hematoxylin and eosin (H&E), Safranin-O, and collagen II staining of the defect cartilage and flat scaffold-, nanobridge scaffold-, stem cell-, and the attached stem cells on the nanobridge scaffold (SC+NS complex) treated cartilage tissue at 3 weeks.

B of FIG. 2 illustrates histological scoring evaluation of the repaired cartilage tissue.

C and D of FIG. 2 illustrate representative scanning electron microscopy (SEM) images of the normal cartilage, regenerated defect, and flat scaffold-, nanobridge scaffold-, stem cell-, and the SC+NS complex treated cartilage tissue.

Error bars represent the standard deviation about the means (n=3 for each group). Data were analyzed by one-way ANOVA (*P<0.05 and **P<0.5).

Figure 3:
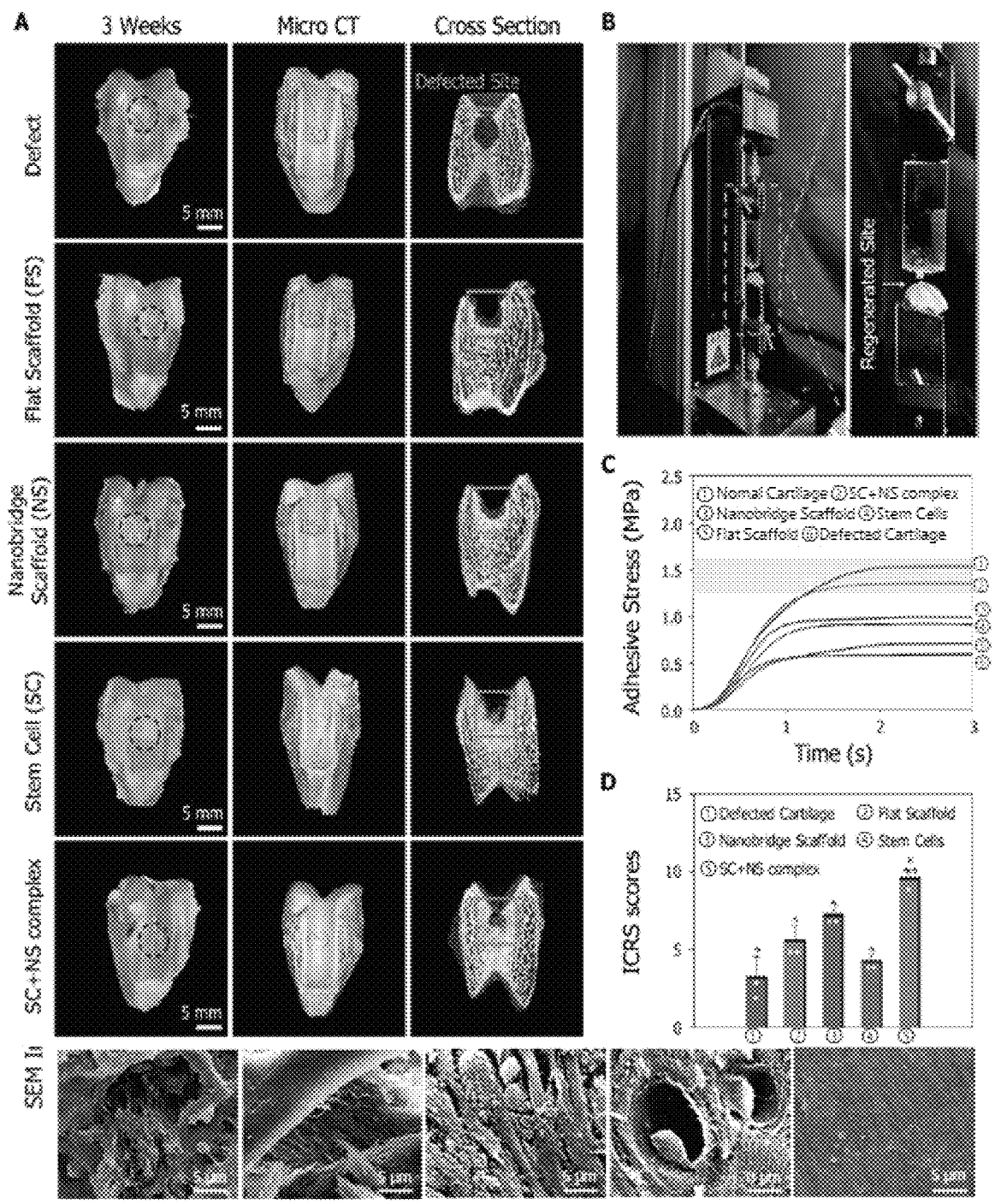

FIG. 3 illustrates effects of the transplantable stem cells nanobridge scaffold on osseocartilaginous regeneration.

A of FIG. 3 illustrates representative macroscopic images and micro-CT images of the defected cartilage and flat scaffold-, nanobridge scaffold-, stem cell-, and the attached stem cells on the nanobridge scaffold (SC+NS complex) treated cartilage tissues at 3 weeks.

B of FIG. 3 illustrates optical images of the custom-built equipment for the adhesion test.

C of FIG. 3 illustrates time-adhesive stress graphs of the defect cartilage and flat scaffold-, nanobridge scaffold-, stem cell-, and SC+NS complex treated cartilage tissues. The colors show the range of the adhesive stress.

D of FIG. 3 illustrates International Cartilage Repair Society (ICRS) histological score of the defected cartilage and flat scaffold-, nanobridge scaffold-, stem cell-, and SC+NS complex treated cartilage tissues.

Error bars represent the standard deviation about the means (n=3 for each group). Data were analyzed by one-way ANOVA (*P<0.05).

Figure 4:
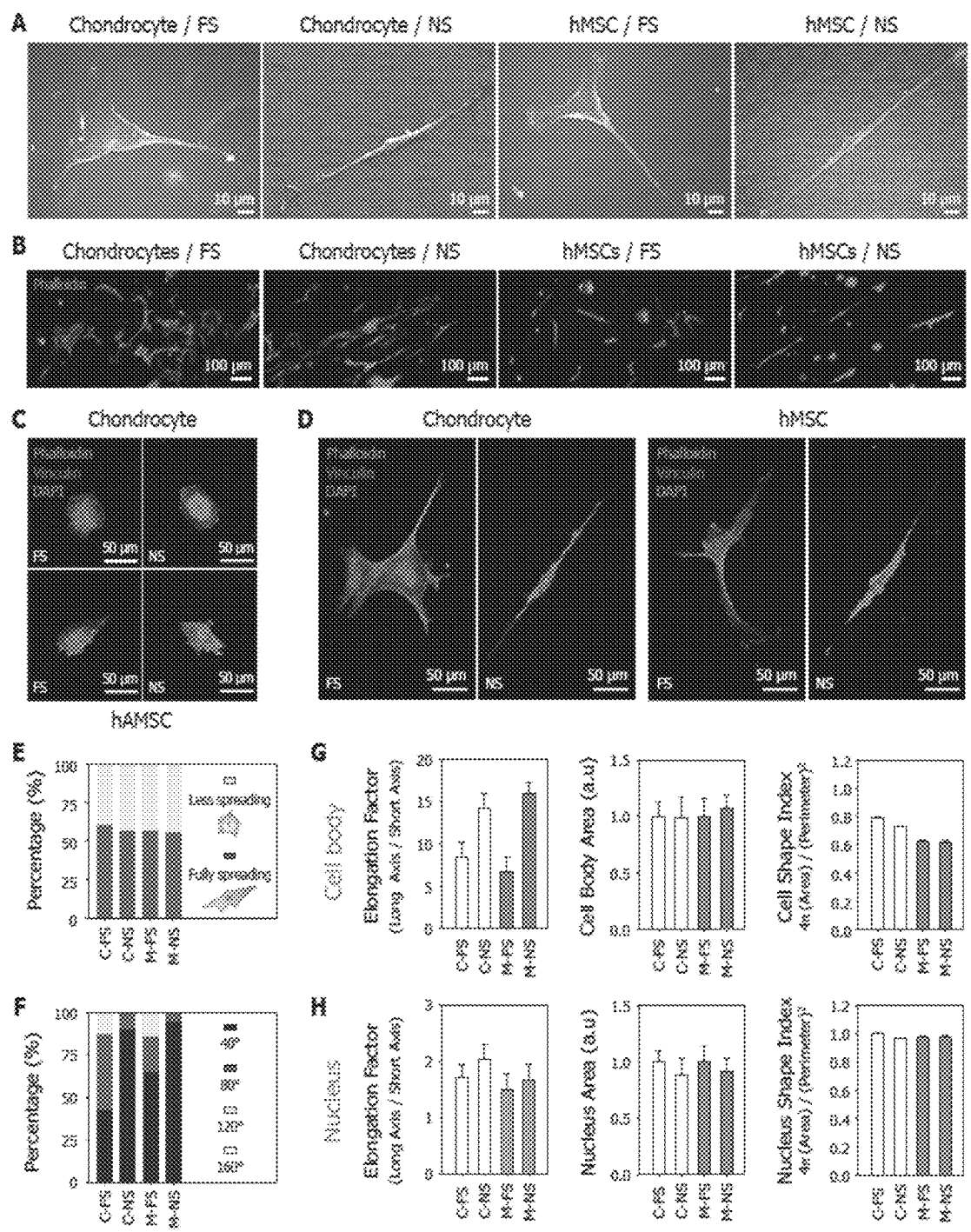

FIG. 4 illustrates effects of the nanotopographical cues on cell morphological responses for cartilage regeneration.

A of FIG. 4 illustrates representative scanning electron microscopy images of chondrocytes (abbreviated as C) and human adipose tissue-derived mesenchymal stem cells (abbreviated as hMSCs or M) on flat (FS) and nanobridge (NS) scaffolds at 12 h.

B of FIG. 4 illustrates immunofluorescence images of the actin cytoskeletons of chondrocytes and hMSCs on the FS and NS at 12 h.

C and D of FIG. 4 illustrate representative immunofluorescence images depicting DAPI (blue), vinculin (green), and F-action (red) staining of less spread and fully spread chondrocytes and hMSCs on the FS and NS.

E of FIG. 4 illustrates quantification of the proportions of less spread and fully spread cells F of FIG. 4 illustrates direction of the fully spread cells on the FS and NS.

G and H of FIG. 4 illustrate quantification of the elongation factors, areas, and shape indexes of the cell body and nucleus of the chondrocytes and hMSCs on the FS and NS.

Error bars represent the standard deviation about the means (n=30 for each group).

Figure 5:
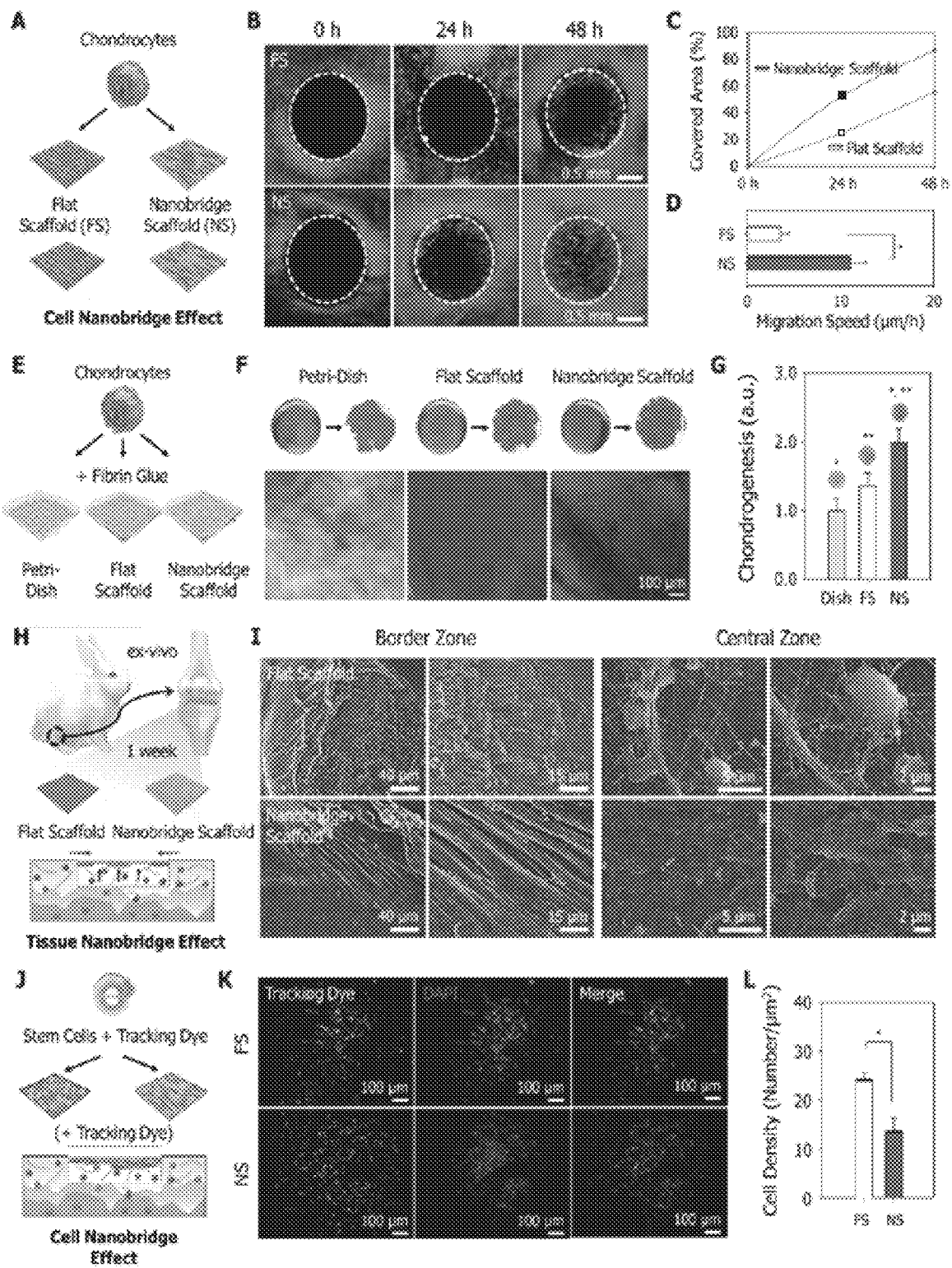

FIG. 5 illustrates effects of the nanotopographical cues on cell migration and confinement for cartilage regeneration.

A of FIG. 5 illustrates schematic of the effects of the flat and nanobridge scaffolds on chondrocyte migration.

B of FIG. 5 illustrates immunofluorescence images (F-actin in red) of chondrocyte migration at 0, 24, and 48 h.

C of FIG. 5 illustrates quantification of the area covered by chondrocytes on the flat and nanobridge scaffolds.

D of FIG. 5 illustrates graph of the migration speeds of chondrocytes on the flat and nanobridge scaffolds (n=4 for each group).

E of FIG. 5 illustrates schematic of the effects of the flat and nanobridge scaffolds on the reconstruction of chondrocytes.

F of FIG. 5 illustrates Alcian blue staining and optical microscopy images of the stained chondrocytes with fibrin glue on a tissue culture plate (TCPS), flat scaffold, and nanobridge scaffold.

G of FIG. 5 illustrates quantification of the chondrogenesis of chondrocytes in fibrin glue on the TCPS and flat and nanobridge scaffolds (n=4 for each group).

H of FIG. 5 illustrates schematic of the effects of the flat and nanobridge scaffolds on cartilage tissue I of FIG. 5 illustrates representative scanning electron microscopy images of the border zone and central zone on the flat and nanobridge scaffolds.

J of FIG. 5 illustrates schematic of the effect of the nanobridge scaffold on cell retention.

K of FIG. 5 illustrates representative fluorescence images of cells (tracking dye: white; nucleus: blue).

L of FIG. 5 illustrates Quantification of the cell densities on the flat and nanobridge scaffolds (n=4 for each group).

Error bars represent the standard deviation about the means. Data were analyzed by one-way ANOVA (*P<0.05).

Figure 6:
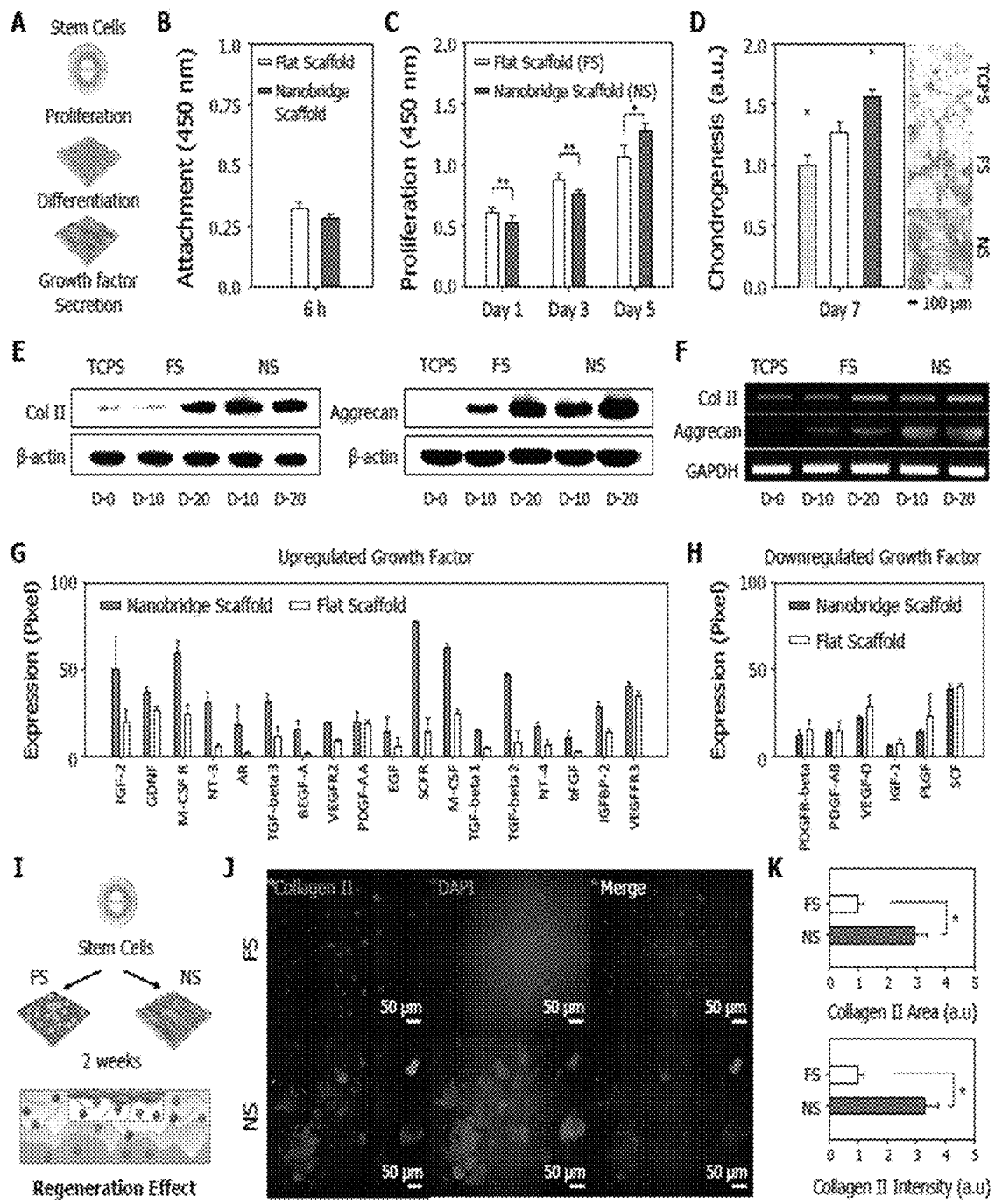

FIG. 6 illustrates effects of the nanotopographical cues on the stem cell functions for cartilage regeneration.

A of FIG. 6 illustrates schematic of the effects of the nanobridge scaffold on stem cell functions.

B of FIG. 6 illustrates attachment of human adipose tissue-derived mesenchymal stem cells (hMSCs) cultured on flat and nanobridge scaffolds for 6 h (n=4 for each group).

C of FIG. 6 illustrates proliferation of hMSCs cultured on flat and nanobridge scaffolds for 1 day, 3 days, and 5 days. Cell attachment and proliferation were quantified using the WST-1 assay, and the absorbance of the samples was measured at 450 nm (n=4 for each group).

D of FIG. 6 illustrates quantification of the degree of chondrogenesis of the hMSCs on flat (FS) and nanobridge (NS) scaffolds as measured using Alcian blue staining; and optical microscopy images of the Alcian blue-stained hMSCs (cell culture: 7 days) (n=4 for each group).

E of FIG. 6 illustrates Western blot analysis of collagen II (Col II) and aggrecan protein expression in hMSCs cultured on flat and nanobridge scaffolds.

F of FIG. 6 illustrates PCR analysis of Col II and aggrecan mRNA expression in hMSCs cultured on flat and nanobridge scaffolds.

G and H of FIG. 6 illustrate expression of upregulated and downregulated growth factors by hMSCs on the flat and nanobridge scaffolds (n=2 for each group).

I of FIG. 6 illustrates schematic of the effect of the nanobridge scaffold on cartilage tissue reconstruction.

J of FIG. 6 illustrates representative immunofluorescence images of collagen II (green) and nuclei (blue)

K of FIG. 6 illustrates Quantification of the collagen II area and intensity (n=4 for each group).

Data were analyzed by one-way ANOVA (*P<0.05 and **P<0.5).

Figure 7:
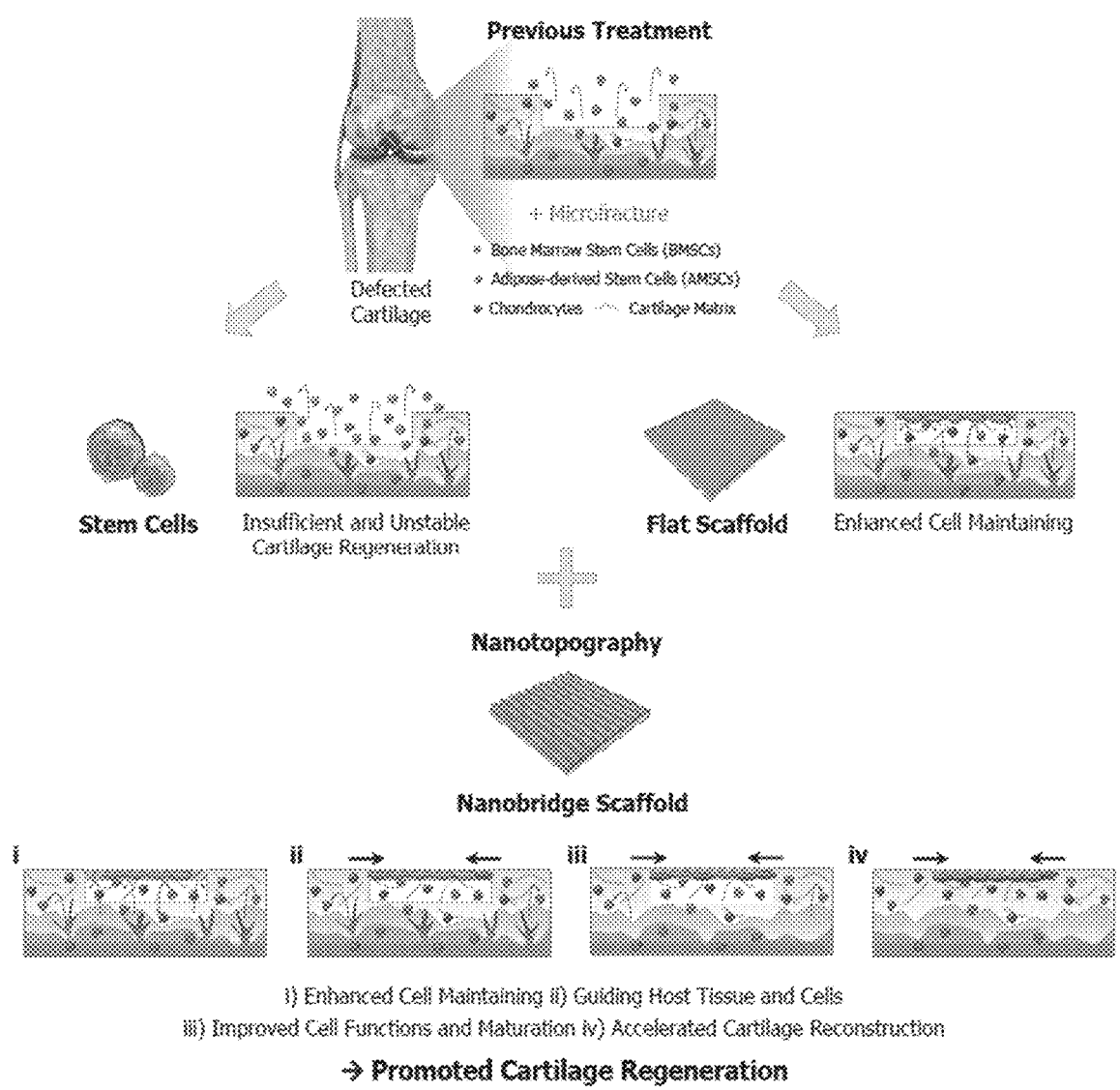

FIG. 7 illustrates summary of the processes through which the stem cells-attached nanobridge scaffold accelerates cartilage regeneration following microfracture surgery.

DETAILED DESCRIPTION

Hereinafter, the present invention will be described in detail.

The present invention may provide a scaffold which includes a plurality of linear nano-patterns and stem cells adhered to the nano-patterns.

By including the plurality of linear nano-patterns aligned in one direction, cells may be aligned/oriented in one direction. Accordingly, regulating specific behavior such as cell migration, cell extension, etc. may control cell tissues and promote regeneration thereof.

As used in the present disclosure, the nano-pattern may have the same meaning as a nano-bridge. The linear nano-patterns may be aligned in one direction, and specifically, aligned in parallel with each other. As used in the present disclosure, the term "parallel" not only means "perfectly parallel" but also includes an alignment that is determined to be "substantially parallel."

The pattern may include a linear pattern and is not particularly limited in the morphology thereof as long as cells are aligned to be oriented by the pattern in a predetermined direction. For example, longitudinal cross-sections may be independently a triangular, rectangular, pentagonal, circular or elliptical shape. In an aspect of more regular cell arrangement, the longitudinal cross-section is preferably in a rectangular form.

The scaffold of the present invention may use any material such as a polymer known in the art without limitation thereto. For example, polyurethane acrylate (PUA) resin, polyvinyl alcohol resin, polyethylene resin, polypropylene resin, polyethyleneglycol resin, poly(L-lactid-co-glycolide) resin, polycaprolactone (PCL) resin, polylactic acid (PLA) resin, polyglycolic acid (PGA) resin, chitosan, gelatin, collagen, etc. may be used alone or in combination thereof. A polymer having non-toxicity and biodegradability as well as biocompatibility, for which the polymer is not degraded till the duration for completion of cartilage regeneration, may be used. Further, in an aspect of biocompatibility, polyurethane acrylate (PUA) resin, polycaprolactone (PCL) resin and/or poly(L-lactide-co-glycolide) resin are preferably used. Alternatively, in an aspect of tissue regeneration, polycaprolactone (PCL) resin is more preferably used, but it is not limited thereto.

A method of forming nano-patterns may include any method known in the art without particular limitation thereof as long as the pattern can be formed using the above-described materials. For example, nano-patterns may be directly plotted by methods such as electronic beam lithography, or self-reassembly using physical properties of a polymer block copolymer that forms a nano-sized pattern by itself or nano-imprinting techniques such as thermal imprinting, UV nano-imprinting, contact imprinting, etc. may be used, but it is not limited thereto.

The nano-pattern may be formed by, for example, placing a mold having patterns formed thereon on a substrate coated with a material as a sample, and then pressing the same, but it is not limited thereto.

A coating method is not particularly limited but may include use of a bar coater, air knife, gravure, reverse roll, kiss roll, spray, blade, die-coater, casting, spin coating or the like.

The mold may be properly selected, for example, a polyurethane acrylate (PUA) mold or a polydimethyl siloxane (PDMS) mold may be used.

The pressing method may include any one commonly used in the art without particular limitation thereof as long as it could be used for patterning.

With regard to the scaffold of the present invention, a width of a ridge and a groove in the nano-pattern is not particularly limited and, for example, may be each independently in a range of 100 to 1000 nm. This may be properly selected so as to have a structure similar to the structure of an extracellular matrix (ECM) of the cartilage (that is, a width similar to ECM pattern). Further, the width of the ridge and the groove may be each independently in a range of 100 to 1000 nm, 200 to 1000 nm, 300 to 1000 nm, 400 to 1000 nm, 500 to 1000 nm, 600 to 1000 nm, 700 to 1000 nm, 800 to 1000 nm, 900 to 1000 nm, or the like, but it is not limited thereto.

With regard to the scaffold of the present invention, a height of the nano-pattern is not particularly limited but may be in a range of, for example, 100 to 1000 nm, 200 to 1000 nm, 300 to 1000 nm, 400 to 1000 nm, 500 to 1000 nm, 600 to 1000 nm, 700 to 1000 nm, 800 to 1000 nm, or 900 to 1000 nm.

With regard to the scaffold of the present invention, the ridge and the groove of the pattern may have nano-pattern topography or nano-topography.

Due to the nano-topography, the scaffold of the present invention may have increased roughness on a surface thereof, and such the increased roughness may also increase shear stress through adhesive force like van der Waals force. Further, the nano-topography may decrease a water contact angle thus to reduce hydrophobic property, thereby improving cell adhesion. The nano-topography may have guidance effects that influence on morphological reaction, proliferation and differentiation of cells so as to improve cartilage regeneration and promote maturation of the cartilage.

In particular, the cells may respond sensitively to nano-topography and exhibit a highly aligned structure according to nano-topography cues.

The scaffold of the present invention may include "stem cells" adhered to the nano-patterns.

The "stem cell" refers to cells having ability of differentiating into various tissues, that is, undifferentiated cells.

The term "differentiation" means a phenomenon in which a structure and function of a cell are specified while the cell grows through division and differentiation, that is, living cells or tissues undergo variation in morphology and functions thereof so that the cells or tissues perform given tasks. Further, the term "undifferentiation" means that the above-described differentiation does not occur. With regard to the object of the present invention, the differentiation may be interpreted as a series of processes in which a stem cell changes to articular chondrocytes.

The stem cell of the present invention is not particularly limited in terms of types and/or origins thereof as long as the stem cell could be differentiated into chondrocytes. Specifically, the stem cell may include mesenchymal stem cells, preferably, human adipose tissue-derived mesenchymal stem cells.

The stem cell may be adhered to the nano-pattern of the scaffold of the present invention.

The stem cell may be adhered to the nano-pattern by any of different methods known in the art. For example, the stem cell may be adhered to the nano-pattern in such a way that: the scaffold may be immersed in a liquid medium containing stem cells; the liquid medium may be poured over the scaffold until the scaffold is covered with the liquid medium; or the liquid medium is added dropwise over the scaffold.

The liquid medium used herein may be any typical medium known to be suitable for stem cell culture in the art. For example, Dulbecco's Modified Eagle's Medium (DMEM) may be used, but it is not limited thereto.

During stem cell culture, not only components required for culturing, but also other components beneficial for stem cell proliferation may be further included. In this case, a constitutional composition of the components and cell culture conditions may be appropriately selected by those skilled in the art.

During treatment using a liquid medium, the treated solution may be standing (or fixed) for a predetermined time so as to adhere the stem cell to the scaffold. For example, the treated solution may be fixed for 6 hours to 7 days, 6 hours to 5 days, 6 hours to 3 days, 6 hours to 1 day, 6 to 18 hours, 6 to 12 hours, 12 hours to 7 days, 12 hours to 5 days, 12 hours to 3 days, 12 hours to 1 day, 12 to 18 hours, 18 hours to 7 days, 18 hours to 5 days, 18 hours to 3 days, 18 hours to 1 day, 1 to 7 days, 1 to 5 days, 1 to 3 day, 3 to 7 days, 3 to 5 days, or 5 to 7 days, but it is not limited thereto.

In the present disclosure, the term "cartilage" is a tissue originated from a mesoderm such as tibia tissues in the embryological aspect, which forms an endoskeleton along with bones, wherein chondrocytes are surrounded by a large amount of extracellular matrixes. The chondrocytes may synthesize the cartilage matrix inside the cartilage and then secrete the same.

The cartilage may be classified into three (3) types including hyaline cartilage, elastic cartilage and fibrous cartilage according to the cartilage matrix. In this regard, the "hyaline cartilage" has a generally matrix which has pale blue and transparent in vivo, is formed of regular tissues on the visual aspect, has a water content of 60 to 80%, and contains mostly Type 2 collagen on the matrix. On the other hand, the "fibrous cartilage" is different from the hyaline cartilage in an aspect of mechanical properties, and contains a large amount of collagen fibers in the matrix so as to have high tension. Further, the fibrous cartilage is enriched with Type 1 collagen in the matrix while having a low content of proteoglycan, thereby involving a deterioration in tolerance to abrasion.

In the case of cartilage regeneration using the scaffold of the present invention, hyaline cartilage may be regenerated.

The scaffold of the present invention may be used to be adhered to a microfracture site of a bone exposed due to cartilage defects.

The term "cartilage defect" means that the cartilage is partially or entirely abraded, damaged or destroyed due to different causes such as external wound, degeneration, auto-immune reaction, etc. In the present disclosure, the cartilage defect may substantially have the same meaning as "cartilage damage."

The microfracture surgery refers to a technique of inducing blood in the bone marrow to flow out of the defected cartilage by perforating fine holes in the bone exposed due to the cartilage defects.

Further, the preset invention may provide a method for treatment of cartilage defects using the scaffold of the present invention which includes a plurality of linear nano-patterns aligned in one direction.

The cartilage defect treatment method of the present invention may include: adhering the scaffold, which includes a plurality of linear nano-patterns aligned in one direction, so that a surface having the nano-patterns formed thereon ("nano-patterned surface") comes into contact with the cartilage defect site of a subject.

The nano-pattern has been described above, and therefore will not be described in detail.

The term "subject" may include an animal with cartilage defects, for example, mammals. The mammals may include dog, cat, pig, cow, rabbit, rat or human, but it is not limited thereto.

The term "cartilage defect site" may include a portion in which a portion or entirety of the cartilage is abraded, damaged or destroyed due to different causes such as external wound, degeneration, auto-immune reaction, etc. The cartilage may be an articular cartilage including a variety of cartilage tissues such as knee cartilage, elbow cartilage, etc.

The scaffold may be adhered so that the nano-patterned surface comes into contact with the cartilage defect site of the subject. When the scaffold is adhered to the cartilage defect site, chondrocytes may migrate faster according to guidance of the nano-pattern. Further, it is possible to coop a specific material up in the cartilage defect site, thereby enhancing cartilage regeneration and maturity.

The material cooped up in the cartilage defect site may include molecules secreted by the stem cells, preferably, a growth factor associated with cartilage regeneration. The growth factor may be highly secreted by the stem cells on a nano-bridge scaffold of the present invention. For example, a transforming growth factor-beta (TGF-beta), stem cell growth factor receptor (SCFR) and macrophage colony-stimulating factor (M-CSF) may be included, but they are not limited thereto.

In the present disclosure, the term "regeneration" means all states in which a portion or entirety of tissues in the cartilage defect site is partially or entirely recovered or repaired. In the present disclosure, the regeneration may have the same meaning as "repair."

The adhesion may be performed so that the nano-patterned surface directly comes into contact with the cartilage defect site. For example, after cutting a skin in which the damaged cartilage is present, the scaffold may be implanted so that the nano-patterned surface directly comes into contact with the cartilage defect site.

In addition, the method of the present invention may further include adhering the stem cells to the nano-pattern of the scaffold.

The stem cells have been described above, and therefore will not be described in detail.

The adhesion of the stem cells to the nano-pattern of the scaffold may be performed before adhering the scaffold to the cartilage defect site.

The adhering method is not particularly limited, as long as the stem cells can be adhered to the nano-pattern. For example, the stem cells may be adhered to the nano-pattern in such a way that: the scaffold may be immersed in a liquid medium containing stem cells; the liquid medium may be poured over the scaffold until the scaffold is covered with the liquid medium; or the liquid medium is added dropwise over the scaffold.

The liquid medium used herein may be any typical medium known to be suitable for stem cell culture in the art. For example, Dulbecco's Modified Eagle's Medium (DMEM) may be used, but it is not limited thereto. During stem cell culture, not only components required for culturing, but also other components beneficial for stem cell proliferation may be further included. In this case, constitutional composition of the components and cell culture conditions may be appropriately selected by those skilled in the art.

During treatment using a liquid medium, the treated solution may be standing (or fixed) for a predetermined time so as to adhere the stem cells to the scaffold. For example, the treated solution may be fixed for 6 hours to 7 days, 6 hours to 5 days, 6 hours to 3 days, 6 hours to 1 day, 6 to 18 hours, 6 to 12 hours, 12 hours to 7 days, 12 hours to 5 days, 12 hours to 3 days, 12 hours to 1 day, 12 to 18 hours, 18 hours to 7 days, 18 hours to 5 days, 18 hours to 3 days, 18 hours to 1 day, 1 to 7 days, 1 to 5 days, 1 to 3 day, 3 to 7 days, 3 to 5 days, or 5 to 7 days, but it is not limited thereto.

Further, the method of the present invention may further include microfracture of the exposed bone on the cartilage defect site, wherein the scaffold may be adhered to the microfractured site.

Specifically, before adhesion of the scaffold to the cartilage defect site, the exposed bone on the cartilage defect site may be perforated to form holes, and this process may be conducted through microfracture surgery well known to those skilled in the art, but it is not limited thereto.

In consideration of damage to cartilage, age and activity level of a subject and so on, the above process may be implemented according to clinical measures. Further, if a marrow component such as blood can leak from the exposed bone on the cartilage defect site toward the damaged cartilage, the microfracture method is not particularly limited but may include any method known in the art unless the exposed bone is completely fractured.

Hereinafter, the present invention will be described in more detail by means of examples. Such examples are proposed only for more concretely illustrating the present invention and the present invention is not limited to the examples.

EXAMPLES

Materials and Methods

1. Fabrication of the Different Scaffolds

The detailed methods for fabricating the PCL scaffolds have already been reported in a previous study. In brief, PCL beads (Mw: 80 000; Sigma-Aldrich, St. Louis, MO, USA) were dissolved in dichloromethane (18 wt % solution), and the solution was then applied for the fabrication of thin PCL films using the spin-coating technique (ACE-200, DongA, Korea). The conditions used were as follows: rotator speed, 3500 rpm; coating duration, 120 s; and acceleration time, 5 s. Then, the irregular surface of each prepared PCL film was melted for 60 s at 80° C., following which PDMS molds were used to create either a flat or a nanotopographical (800 nm, ridges and grooves) pattern on the melted film surface under pressure at 80° C. for 2 min. After the nanobioimprinting process, the assembly was cooled at room temperature for 30 min. Then, the PDMS mold was removed from the PCL film, resulting in either the nanopatterned (nanobridge) scaffold or flat scaffold.

2. Characterization of the Fabricated Scaffolds

The structures of the scaffolds were evaluated using a JSM-7500F field emission scanning electron microscope (JEOL Ltd., Tokyo, Japan). The surfaces were analyzed with an atomic force microscope (XE-100, Korea). The chemical bonds were confirmed by FTIR spectroscopy (Spectrum 400). The mechanical properties were analyzed with an MCT 1150 system (AND, Korea). The contact angles were measured using ImageJ software (NIH, Bethesda, MD, USA).

3. In Vivo Animal Study

All New Zealand white rabbits were purchased from Damul Science (Daejeon, Korea). A chondral defect model was created in 34 eligible rabbits (3-3.5 kg, 3 months old) for evaluating the recruitment, fixation, and regeneration effects of the hMSCs and the hMSCs-nanobridge complex. After general anesthesia, chondral defects (3 mm diameter, 1 mm height) were created on the patellar surface of the femur of the knee according to the "Standard Guide for in vivo Assessment of Implantable Devices Intended to Repair or Regenerate Articular Cartilage" published by the American Society for Testing and Materials.

4. Histological Evaluations

The cartilage specimens were fixed in 10% neutral buffered formalin (pH 7.4) and decalcified with Calci-Clear Rapid (National Diagnostics, Atlanta, GA, USA) for 2 weeks, then dehydrated with a graded series of ethanol solutions (80%, 90%, 95%, and 100% v/v), and finally embedded in paraffin blocks. Sections of 4-5 µm thickness were cut from the blocks with a microtome and subjected to hematoxylin and eosin, Safranin-O, and immunohistochemical staining analyses. To confirm the expression of collagen II, the sections were first treated with 3% $H_2O_2$ and Triton X-100 and then blocked with 1% bovine serum albumin (BSA). Thereafter, the samples were reacted with a mouse monoclonal anti-rabbit antibody against collagen II (1:300 dilution; Novus Biologicals, Centennial, CO, USA) for 1 h. This was followed by incubation with a horseradish peroxidase-conjugated goat anti-mouse secondary antibody (1:300; Novus Biologicals) for 1 h. Subsequently, the samples were reacted with the solutions in the Vectastain ABC Kit (Vector Laboratories, Burlingame, CA, USA) for 50 min and developed with the reagents in the DAB Substrate Kit (Vector Laboratories) for 7 min. The stained samples were examined under a Lionheart FX automated microscope (BioTek, Winooski, VT, USA).

5. Scanning Electron Microscope Imaging hMSCs and chondrocytes were separately cultured on the flat and nanobridge scaffolds for 2 h. Thereafter, the cells attached on the scaffolds were fixed with 2% paraformaldehyde (Sigma-Aldrich) and 2% glutaraldehyde (Sigma-Aldrich) in 1×phosphate-buffered saline (PBS) (Sigma-Aldrich) for 4 h and then washed three times with 1×PBS. Then, the fixed cells were treated with 1% osmium tetroxide (Sigma-Aldrich) for 1.5 h, washed three times with 1×PBS, and dehydrated with a graded series of ethanol solutions (30%, 50%, 70%, 80%, 90%, and 100% v/v). The samples were finally coated with a Pt layer (~5 nm thick) by metal sputtering, and images of the cells were obtained using a JSM-7500F field emission scanning electron microscope (JEOL Ltd.).

6. Immunofluorescence Staining hMSCs and chondrocytes were separately cultured on the flat and nanobridge scaffolds for 12 h. Thereafter, the attached cells were fixed with 4% paraformaldehyde (Sigma-Aldrich) for 5 min and washed three times with 1×PBS. The fixed cells were reacted with 0.1% Triton X-100 in 1×PBS for 10 min and washed three times with 1×PBS. Then, the cells were blocked with 1% BSA for 1 h and subsequently stained overnight at 4° C. with the BSA-diluted anti-vinculin primary antibody (Sigma-Aldrich). After washing three times with 1×PBS, the cells were reacted with the PBS-diluted fluorescein isothiocyanate- and tetramethylrhodamine-conjugated phalloidin secondary antibody (Sigma-Aldrich). After washing three times with 1×PBS, the cell nuclei were stained with diluted 4,6-diamidino-2-phenylindole (Sigma-Aldrich). The stained cells were observed with a laser confocal scanning microscope system (TCS SP5/AOBS/Tandem, Leica, Wetzlar, Germany). Quantification of the cell nuclei and bodies was carried out using ImageJ software.

7. Cell Attachment and Viability Analyses

For the in vitro studies, human adipose tissue-derived mesenchymal stem cells (hMSC-ad, Cat. No. 19382) and human chondrocytes (HC-a, Cat. No. 6884) were purchased from ScienCell Research Laboratories (San Diego, CA, USA). To evaluate the attachment and viability of the hMSCs on the different scaffold samples, $1\times10^3$ cells/sample were cultured in normal Dulbecco's modified Eagle's medium (DMEM) (Sigma-Aldrich) containing 10% fetal bovine serum (Sigma-Aldrich) and 1% antibiotics (Sigma-Aldrich) for 6 h, 1 day, 3 days, and 5 days at 37° C. under a humidified atmosphere with 5% $CO_2$. The quantification of cell viability was performed using the WST-1 assay (PreMix WST-1 Cell Proliferation Assay System, TaKaRa, Kusatsu, Japan) and the treated cells were analyzed with a UV-visible spectrophotometer and absorbance reader (iMark Microplate Absorbance Reader, Bio-Rad Laboratories, Hercules, CA, USA).

8. Chondrogenesis

To evaluate the chondrogenesis of the hMSCs on the two different scaffolds, $1\times10^4$ cells/sample were cultured for 7 days in chondrogenic differentiation medium (Promo Cell, Heidelberg, Germany). Thereafter, the cells were stained with an Alcian blue solution (1% Alcian blue powder in 3% acetic acid; Sigma Aldrich) and destained with 0.1 M HCl (Sigma-Aldrich). The degree of chondrogenesis was determined using an iMark microplate absorbance reader at 562 nm.

9. Western Blotting

To confirm the protein expression levels of collagen II and aggrecan, hMSCs were first cultured on the two scaffolds for 12 h, following which $1\times10^5$ cells/sample were cultured in chondrogenic differentiation medium (Promo Cell) for 20 days. Thereafter, the cells were washed twice with cold PBS and lysed by ultrasonication in RIPA buffer for 30 min at 4° C. The lysates were collected by centrifugation at 12,000×g for 15 min at 4° C. After washing the cells twice with cold PBS, they were lysed again with a modified RIPA buffer (150 mM sodium chloride, 1% Triton X-100, 0.5% sodium deoxycholate, 0.1% sodium dodecyl sulfate (SDS), 50 mM Tris (pH 8.0), 1 mM phenylmethylsulfonyl fluoride, 2 µg/mL leupeptin, 1 µg/mL pepstatin, 1 mM sodium orthovanadate, and 100 mM sodium fluoride) for 30 min at 4° C. The lysates were cleared by centrifugation at 14,000×g for 15 min at 4° C. The protein content of the cell lysates was determined using the Micro BCA Assay Kit (Pierce, Rockford, IL, USA) according to the manufacturer's instructions. Thereafter, equivalent amounts of protein were separated by 10% SDS-polyacrylamide gel electrophoresis, and the bands were electrophoretically transferred to a polyvinylidene difluoride membrane. After blocking the membrane in 5% non-fat milk at room temperature for 1 h, the blots were incubated overnight with anti-collagen II, anti-aggrecan, and anti-beta-actin antibodies (Santa Cruz Biotechnology, CA, USA). Horseradish peroxidase-conjugated anti-rabbit and anti-mouse antibodies (Santa Cruz Biotechnology) were used as the secondary antibodies. The protein bands were detected using an enhanced chemiluminescence kit (Elpis Biotech Inc., Daejeon, Korea) and exposed to radiographic film. Prestained blue markers were used for the molecular weight determination.

10. RNA Isolation and Quantitative Reverse-Transcription Polymerase Chain Reaction Analysis RNA was isolated from the samples using the TRIzol reagent (Sigma-Aldrich) according to the manufacturer's instructions. The RNA concentration was estimated spectrophotometrically with a BioTek microplate reader (Synergy HTX, KR) at A260/280. The RNA samples were then reverse transcribed into first-strand cDNA using the AccuPower RT PreMix (Bioneer, Daejeon, Korea). The primer sequences used for the reverse-transcription polymerase chain reaction were as follows: 5'-TTCAGCTATG-GAGATGACAATC-3' (SEQ ID NO: 1) and 5'-AGAGTCCTAGAGT GACGAG-3' (SEQ ID NO: 2) for alpha-1 type II collagen (COL2A1); and 5'-GAAGGT-GAAGGTCGGAGTCA-3' (SEQ ID NO: 3) and 5'-GAA-GATGGTGATGGGATTTC-3' (SEQ ID NO: 4) for glyceraldehyde-3-phosphate dehydrogenase (GAPDH). All the primers were confirmed to be specific to only the human gene, and the transcript levels were normalized to that of GAPDH.

11. Growth Factor Array

To evaluate the types and quantities of growth factors secreted by the hMSCs on the two scaffolds, $1\times10^6$ cells/sample were seeded on the substrates and cultured for 3 days in the chondrogenic differentiation medium. The cells were then cultured in DMEM for one additional day. The DMEM from the culture was then reacted with the reagents in the RayBio C-Series Human Growth Factor Antibody Array C1 Kit (RayBiotech, Norcross, GA, USA) according to the manufacturer's protocol. In brief, the kit membrane was first reacted with blocking buffer for 30 min and then incubated with the culture DMEM containing the secreted growth factors for 4 h at room temperature. After washing three times with the kit-provided wash solution, the membrane was treated with a biotinylated antibody cocktail for 2 h and then washed several times with the wash solution. The membrane was then treated with horseradish peroxidase-conjugated streptavidin for 2 h. Following several more washes with the wash solution, the growth factor-labeled membrane was analyzed using a ChemiDoc XRS+ system (Bio-Rad).

12. Migration Assay

To evaluate the guidance effects of the nanopatterned and control flat surfaces on the chondrocytes, a thin PDMS barrier slab (500 µm diameter) was used to form a cell-free area. Then, chondrocytes ($1\times10^6$ cells/sample) were cultured on the scaffolds. After cell attachment, the PDMS slabs were removed manually with sharp tweezers. Migration of the chondrocytes into the circular zone was observed at 0, 24, and 48 h by immunostaining of the cell cytoskeleton and confirmed by observation under a fluorescence microscope (Zeiss, Oberkochen, Germany). The area of cell coverage was analyzed with ImageJ software.

13. Chondrogenesis in 3D Cultures

To evaluate the effects of the nanopatterned and control flat surfaces on chondrogenesis in a 3D environment, chondrocytes ($1\times10^3$ cells/sample) were first cultured on the different scaffolds. After cell attachment for 3 h, fibrin glue was added to the surfaces and the various systems were cultured in chondrogenic differentiation medium for 7 days. Thereafter, the samples were fixed with 4% paraformaldehyde for 5 min, following which the cells were treated with Alcian blue solution (1% Alcian blue powder in 3% acetic acid solution). After destaining with 0.1 M HCl, the degree of chondrogenesis was quantified with an iMark microplate absorbance reader at 562 nm.

14. Statistical Analysis

Student's t-test was used to compare two different conditions. To compare three or more conditions, one-way analysis of variance was performed. In all cases, P values of less than 0.05 were considered statistically significant. All quantitative results are presented as the mean±standard deviation.

Results

1. Design and Fabrication of the Transplantable Nanobridge Scaffold

To maximize cartilage regeneration using the microfracture technique, the cornerstone of the proposed approach is a nanobridge scaffold composed of an array of regularly spaced aligned nanopatterns. The nanobridge scaffold was based on the following rational design standards: i) it had to be composed of a biodegradable and biocompatible material to give the healing cells unrestricted access to the injury site during cartilage restoration (or regeneration); ii) it had to be transplantable and freestanding to both deliver the stem cells into the body and confine them along with their cartilage-related molecules; iii) it had to provide a cartilage tissue-like environment for promoting the functions of the stem cells and chondrocytes without any disruption; and iv) it had to have a topography that could guide the cells through nanopatterned cues and bridge the gap between the host tissue and damaged tissue (A of FIG. 1). Because cartilage regeneration takes more than 8 months to complete, the biocompatible, nontoxic, and biodegradable polymer PCL, which has a degradation time of over 24 months, was used as the nanobridge substrate.

First, a PCL solution was spin-coated onto a glass surface for glass transition temperature-based separation. Then, using a nanobioengineered imprinting technique, heat and pressure were applied to fabricate transplantable PCL scaffolds and to form either a cartilage superficial zone-inspired nanopattern (ridges and grooves: 800 nm; depth: 800 nm; nanobridge) or a flat pattern on the scaffold surface (B of FIG. 1). As shown in C of FIG. 1, the resulting nanobridge scaffold had a sophisticated nanopattern of high aspect ratio arranged regularly on the surface, whereas the flat scaffold had a planar surface without the crystalline structure of PCL. The fabricated nanopatterned scaffolds were freestanding and flexible units that could be used as a transplantable stem cell scaffold, acting as a nanobridge. The structures of the prepared PCL-based scaffolds were confirmed by atomic force microscopy, and they were determined to have the following roughness values: arithmetic average roughness (Ra)=36.5273 nm and root mean squared roughness (Rq)=44.6758 nm for the flat scaffold; and Ra=285.8996 nm and Rq=311.3839 nm for the nanobridge scaffold, indicating that the formation of nanogroove on the flat substrate affected on the increased roughness of the surfaces.

The increased roughness of the nanobridge scaffold surface increased its shear stress (i.e., 16.3 MPa vs. 12.3 MPa for the flat scaffold) (I of FIG. 1) because of the adhesive force like van der Waals of nanopatterned substrates. In addition, it decreased its water contact angle (i.e., 68.19° vs. 76.24° for the flat scaffold) (J of FIG. 1) due to expanded surface area of nanogroove. The increased stress adhesion of the nanobridge scaffold to the cartilage would enable its successful implantation into the surrounding tissue, whereas its decreased hydrophobicity would improve cell attachment, given the general finding that a high degree of hydrophobicity decreases cell attachment. Fourier-transform infrared (FT-IR) spectroscopy analysis of the prepared scaffolds indicated peaks at 1161 $cm^{-1}$ (indicative of the deformation of C—O), at 1720 cm-1 (indicative of the C═O stretching vibration), and near 2900 and 2950 $cm^{-1}$ (indicative of $CH_2$ asymmetric stretching) (G of FIG. 1). The Raman spectra of the scaffolds revealed the crystalline fractions at 1270-1320 $cm^{-1}$ ($\omega CH_2$), 1405-1470 cm-1 ($\delta CH_2$), 1710-1750 $cm^{-1}$ (C═O), and 2800-3200 $cm^{-1}$ (vCH) (H of FIG. 1). These findings demonstrated that the two types of prepared PCL scaffolds had the same chemical properties but different structural properties that affected their roughness, stress adhesion, and hydrophilicity.

2. Cartilage Tissue-Regenerating Effects of the Nanobridge Scaffold and Stem cells (1) Histological and Surface Evaluations To reveal the dual effects of the nanobridge scaffold and stem cells, in vivo studies were investigated. The microfracture technique, which is regarded as the gold standard for cartilage repair, was carried out in vivo on the patellar surface of the femur of the knees of New Zealand white rabbits before implantation of the prepared PCL-based scaffolds (i.e., nanobridge scaffold (NS) and flat scaffolds (FS)) to maximize the effects of the nanobridge scaffold. In addition, fibrin glue mixed stem cell (SC) treatment with microfracture, which is emerged treatment technique, was conducted as the positive control. In order to confirm effects of a nano-bridge scaffold for cartilage regeneration based on stem cells, the stem cells were adhered to a nano-pattern of the nano-bridge scaffold by the following methods.

The liquid medium used herein was Dulbecco's Modified Eagle's Medium (DMEM, Sigma-Aldrich) including 10% bovine fetal serum (Sigma-Aldrich) and 1% antibiotics (Sigma-Aldrich).

Under specific culture conditions (37° C., 5% $CO_2$ humidified environments), a liquid medium including stem cells was poured over the nano-bridge scaffold exposed to atmosphere until the scaffold is covered with the liquid medium.

The stem cells were adhered to nano-patterns of the nano-bridge scaffold and cultured. Before adhesion of the scaffold to the cartilage defect site, that is, immediately before microfracture surgery, the scaffold was taken out of the liquid medium, followed by flowing liquid. The nano-bridge scaffold having the stem cells adhered thereto (a composite of SC and NS) was adhered to the cartilage defect site.

Macroscopic observation of the defect sites revealed no obvious immunological or inflammatory complications after the surgery (A of FIG. 2). At postoperative week 3, the histological images showed that the untreated defects with the microfracture alone had not regenerated, and there was a vacant space around the defect site caused by the fibrin glue fragments (A of FIG. 2). Compared with the defect model, the flat scaffold- or stem cell-treated models were partially repaired, showing a tough surface and distinct borders with the native cartilage tissue. Interestingly, although the macroscopic images of the models treated with the nanobridge scaffold alone or with the stem cells plus nanobridge scaffold complex showed regenerated cartilage tissue surfaces like those of the native cartilage, the immunohistochemical images revealed that the SC+NS complex had resulted in a significantly thicker layer of regenerated cartilage tissue. Compared with the defect treated with microfracture surgery alone, the cartilage treated with SC+NS complex had wider and denser red-colored staining, which was indicative of active cartilage repair. Moreover, the SC+NC complex-treated tissue was strongly positive for collagen II, indicating the presence of hyaline cartilage. As evident from the histological images, the defect border of the cartilage treated with the nanobridge scaffold alone had begun to disappear, indicating the guidance provided by the nanoaligned pattern from the host tissue to the defected tissue. the Furthermore, the defect treated with the SC+NS complex had even better tissue regeneration, with thick hyaline cartilage formation. Based on histological observations, the cartilage with SC+NS complex exhibited the enhanced cartilage regeneration of a higher histological score compared with the other groups (B of FIG. 2). Scanning electron microscopy (SEM) of the regenerated cartilage site was carried out to confirm its morphological structure. It is known that normal cartilage tissue has a planar surface, and its collagen fibers are assembled in parallel to the cartilage (C of FIG. 2). The surface of the defected cartilage treated with microfracture surgery alone had a completely disordered structure, and the collagen fibers were not aligned (D of FIG. 2). By contrast, the surface of the regenerated cartilage treated with SC+NS complex displayed relatively minor superficial splits and had a nanobridge-like appearance. The surface of the cartilage treated with stem cells alone had a gel-like porous structure, with the cells appearing shrunken in the holes as a result of the filled fibrin glue with cells. Interestingly, the regeneration of the flat scaffold-treated cartilage appeared to be fast and stable, but the nanobridge-treated cartilage showed a denser and more ordered fiber structure in parallel to the cartilage. This suggested that the nanotopographical cues of the nanobridge scaffold had a beneficial effect on tissue reconstruction, and the stem cells had a further positive effect on the compact cartilage regeneration.

(2) Micro Computed Topography and Mechanical Property Evaluations

To confirm the reconstruction of the osteochondral defect with the microfracture technique, micro computed tomography (micro-CT) imaging was performed, and 3D and cross-sectional images showing the differences in the regenerated defect sites and trabecular microarchitectures according to the various treatments were obtained. As shown in A of FIG. 3, the defect created by the microfracture surgery was still evident after 3 weeks, and the regeneration of the defect in the flat scaffold-, nanobridge scaffold-, and stem cell-treated cartilage tissue (all with a distinct border) was slower than that of the SC+NS complex treated cartilage tissue (with a vague border). Unlike the scaffold-treated cartilages that regenerated from the host tissue near the defect site, the stem cell-treated cartilage was repaired irregularly. To analyze the mechanical properties of the regenerated cartilage tissues, the adhesive bonding stress test was performed in detail by measuring the adhesion force at specific surfaces of the regenerated cartilage tissue using custom-built equipment (B of FIG. 3). The adhesive stress value for normal cartilage tissue was approximately 1.5 MPa, whereas that for the defected cartilage tissue was 0.5 MPa, indicating insufficient cartilage tissue reconstruction (C of FIG. 3). Unlike the micro-CT results, the stress test results showed that the stem cell-treated cartilage tissue had significantly decreased adhesive stress, being similar to the mechanical property of the defected cartilage tissue. In other words, the stem cell-treated cartilage looks like a successful regeneration, but it could not have physical function like normal cartilage properly. The scaffold-treated cartilage tissue had slightly increased adhesive stress values (>0.9 MPa for the nanobridge scaffold-treated tissue and >0.8 MPa for the flat scaffold-treated tissue). Interestingly, the mechanical properties of the cartilage with the stem cells-treated nanobridge scaffold have a similar result of the mechanical properties of the normal cartilage, suggesting the stem cells-treated nanobridge scaffold can be provided the suitable environment for the formation of the mature cartilage tissue. Finally, the inventors evaluated the macroscopic appearance and quality of the various treated tissues according to the International Cartilage Research Society histological score, whereupon the scores for the SC+NS complex treated cartilage were shown to be significantly different to those for the other groups (D of FIG. 3). These findings suggested that the SC+NS complex was highly effective for cartilage regeneration and could promote the maturity of the defected cartilage.

3. Cell Morphological Response to Nanobridge Cues for Cartilage Tissue Regeneration According to our in vivo studies above, the nanobridge scaffold-treated cartilage tissue showed enhanced regeneration, like that of normal cartilage tissue, and cartilage formation was synergistically promoted by the incorporation of stem cells onto the nanobridge scaffold. In the superficial zone of articular cartilage, the ECM-containing collagen fibers exist with well-organized nanoscale proteins, which are naturally oriented in certain directions. It is known that naturally anisotropic ECM nanostructures can control the morphology of cells and affect their behavior. Guided by these considerations, the inventors prepared the nanobridge and demonstrated its effect on the morphological responses of various cells, using hMSCs as attached cells and chondrocytes as host cells. The hMSCs and chondrocytes were cultured separately on both the flat and nanobridge scaffolds for 12 h and then visualized by SEM and immunofluorescence staining. As shown in A of FIG. 4, the hMSCs and chondrocytes had reacted sensitively to the nanotopographical structure, with both types of cells being highly aligned in one direction. They also had different spreading patterns, showing either fully or less spread cells on the two different types of scaffolds (B to D of FIG. 4). Classification of the type of spreading of the cells and their quantification revealed no significant differences among the various groups, with the less spread cells accounting for over 35% of all cells (E of FIG. 4). Next, the direction of the fully spread cells on the flat and nanobridge scaffolds was quantified. The hMSCs and chondrocytes had an aligned structure on the nanobridge scaffold, unlike the cells on the flat scaffold, with the stem cells being slightly more sensitive to the nanotopographical cues than the chondrocytes (95% for hMSCs vs. 90% for chondrocytes) (F of FIG. 4). The elongation factor (EF, defined as major axis/minor axis), area, and shape index (SI, defined as $4\pi \times area/perimeter^2$) of both the nuclei and cell bodies were also estimated in all the cell groups on the various scaffolds. The EFs of the cell bodies and nuclei were highly increased by the nanobridge scaffold, with the cell body being more sensitively affected by the nanotopographical cues than the nucleus (F of FIG. 4). Although there were no significant differences in the cell body area, nucleus area, and nucleus SI among the groups, the cell SI results indicated that the cells on the nanobridge scaffold had lost their spread structure. Taken together, the optical and SEM images and quantitative results of cell morphology demonstrated that the hMSC and chondrocyte shapes and structures were susceptible to and could be regulated by the nanotopography of the nanobridge scaffold.

4. Effects of Nanobridge Cues on Cell Migration and Confinement

Our in vivo studies demonstrated that the transplantable nanobridge scaffold with its aligned nanostructures could significantly improve the regeneration of damaged cartilage tissues, promoting the tissue reconstruction in the rabbit model. The surface of the regenerated cartilage had an aligned structure similar to that of the cartilage superficial zone-inspired nanotopography of the nanobridge, indicating that cartilage regeneration was highly affected by the nanotopography. To reveal the possible mechanism underlying this effect, the inventors hypothesized the main factors for the nanobridge-based cartilage regeneration to be as follows: i) the host tissue and cells might have migrated along the guidance of the nanobridge; ii) the implanted and microfracture-generated stem cells were maintained in the cartilage defect location by the flexible nanobridge scaffold; iii) the differentiation and maturation of the stem cells were affected by the nanotopographical cues of the nanobridge; and iv) the combination of all three above-mentioned effects could have promoted tissue regeneration and restoration by optimizing the body's own resources. During cartilage repair with the implantation of scaffolds, it is difficult for the mature chondrocytes in the host tissue to migrate and proliferate, causing late cartilage regeneration from the lower self-repair capability. To reveal the guidance effect of the nanopatterned topography in vitro, a thin circular slab of polydimethylsiloxane (PDMS) was first placed on the flat and nanopatterned scaffolds and chondrocytes were then cultured on the substrates for 1 day (A of FIG. 5). Then, by removing the PDMS slab, the migration of the chondrocytes at the perimeter of the circled area into the empty space could be confirmed through immunostaining imaging (B of FIG. 5). After 24 h, the chondrocytes on the nanobridge scaffold had migrated to the central part of the circle, whereas the cells on the flat scaffold remained close to the original circular perimeter. Thus, at this point, the area of migration by the chondrocytes on the nanobridge scaffold was twice that by the cells on the flat scaffold (i.e., 52.0% vs. 25.3%, respectively). After 48 h, the chondrocytes on the nanobridge scaffold had filled most of the empty surface, displaying a faster migration speed than that of the cells on the flat scaffold (86.5% vs. 52.6% migration area, respectively) (C of FIG. 5). The migration speed of the chondrocytes was quantified according to the methods of a previous study, whereupon it was shown to be three times faster on the nanobridge scaffold than on the flat scaffold (12.99 μm/h vs. 4.14 μm/h, respectively) (D of FIG. 5). Additionally, the maturation of the chondrocytes is very important, as the molecules that they secrete can promote the reconstruction of the defected cartilage. Thus, the ability of the chondrocytes to reconstruct the cartilage matrix was evaluated. To fabricate the 3D environment, injectable fibrin glue was applied to the chondrocytes attached onto the nanobridge and flat scaffolds (E of FIG. 5). Then, following treatment with the chondrogenic differentiation medium, the degree of chondrogenesis (in arbitrary units [a.u.]) was quantified using Alcian blue staining. Surprisingly, chondrogenesis in the fibrin glue added to a traditional tissue culture polystyrene dish (TCPS) was significantly different to that in fibrin glue added to the scaffolds (TCPS vs. flat scaffold vs. nanobridge scaffold=1 vs. 1.35 vs. 1.98 a.u., respectively). The fibrin glue on the nanobridge scaffold had the bluest color, indicating a higher degree of chondrogenesis with better infiltration of the chondrocytes (F and G of FIG. 5). These finding revealed that the enhanced reconstruction of the cartilage matrix on the nanobridge scaffold with the nanopatterned topography had promoted the maturation of the chondrocytes.

The in vivo and in vitro results obtained so far had revealed the great potential of the nanopatterned scaffold as a nanobridge for promoting cartilage regeneration and chondrogenesis. Additionally, the inventors attempted to reveal the guidance effect of the nanobridge on tissue ex vivo; therefore, the SC+NS complex were implanted onto defected cartilage tissues. After 1 week, the structure of the surfaces was confirmed by SEM (H of FIG. 5). As shown in I of FIG. 5, the host cells had migrated to the scaffolds, and a cartilage tissue-like matrix had formed near the border zone. Unlike that on the flat scaffold, the ECM had integrated with the nanotopography of the nanobridge scaffold, displaying increased integration and reconstruction from the marginal host cartilage tissue. Although the nanotopography on the border zone of the nanobridge was maintained, that on its central zone had mostly crumbled. This was likely because ECM molecules from the attached stem cells had blended with the nanotopography, filling up the grooves. By contrast, the surfaces of the flat scaffold were covered with fibrous ECM molecules, displaying uneven and rough structures. Next, the inventors investigated the abilities of the various scaffolds in maintaining the stem cells, because this is an important factor to ensuring they provide continual cartilage regeneration functions (J of FIG. 5). Stem cells with a tracking dye were adhered onto the flat and nanobridge scaffolds and their retention on the scaffolds was confirmed using fluorescence microscopy. To confirm the maintained stem cells, the inventors quantified the stem cell density using fluorescence microscopy images. More stem cells were retained on the nanobridge, whereas they were more densely attached on the flat scaffold ($13.7/\mu m^2$ vs. $24.3/\mu m^2$ on the flat scaffold) (K and L of FIG. 5). As a result, the cartilage tissue that was regenerated by treatment with the nanobridge had a uniform surface, thereby allowing improved solid reconstruction.

5. Effects of Nanobridge Cues on Stem Cell Functions

Because of the differences in cell morphology between the flat and nanobridge scaffolds, the inventors hypothesized that the nanotopographical cues could be responsible for the enhanced cellular behavior related to cartilage regeneration. First, the inventors investigated the effects of the nanobridge on stem cell attachment, proliferation, differentiation, and growth factor secretion (A of FIG. 6). After 6 h of culture, it was confirmed that there was no significant difference between the two scaffolds in terms of cell attachment (B of FIG. 6). After 1 day and 3 days of culture, the hMSCs on the nanobridge scaffold showed slightly lower proliferation than those grown on the flat scaffold, but this situation was reversed after 5 days of culture (C of FIG. 6). These results indicate that the nanobridge scaffold does not inhibit the proliferation of cells on its surface and could in fact induce their growth. Next, hMSCs attached to flat or nanobridge scaffolds were cultured in chondrogenic medium for 7 days, and the degree of chondrogenesis was quantified using Alcian blue staining. As shown in D of FIG. 6, the inventors confirmed a higher degree of hMSC chondrogenesis on the nanobridge scaffold than on the flat scaffold and TCPS. To further verify the improved chondrogenesis on the nanobridge scaffold, the expression of the early-stage cartilage matrix gene coding for collagen II and the matrix gene coding for aggrecan was evaluated by western blot and quantitative reverse-transcription polymerase chain reaction assays. None of these genes were expressed by the hMSCs on TCPS on day 0, but gene expression by the cells on the flat and nanobridge scaffolds improved as the days progressed. Importantly, chondrogenesis was significantly promoted by the nanotopographical cues of the nanobridge, with collagen II being expressed more quickly on this scaffold than on the flat one (E and F of FIG. 6). The chondrogenic capacity of hMSCs might be related to the substrates (e.g., nanotopography of the nanopatterned scaffold), with the nanobridge offering the most suitable conditions for the formation of the cartilage matrix.

It is known that stem cells generate autocrine and paracrine factors, which are crucial signaling molecules for activating various cellular functions. Therefore, the inventors investigated the secretion of growth factors from hMSCs cultured on the nanobridge scaffold, as the inventors speculated that the nanotopographical cues could affect autocrine and paracrine signaling to cells. Compared with the hMSCs on the flat scaffold, the cells on the nanobridge scaffold secreted higher levels of all the growth factors tested, especially transforming growth factor-beta (TGF-beta), stem cell growth factor receptor (SCFR), and macrophage colony-stimulating factor (M-CSF). TGF-beta and M-CSF are the representative growth factors for cartilage regeneration, with the former affecting all stages of chondrogenesis through the accumulation of cartilage-related ECM molecules. M-CSF also induces proteoglycan synthesis, another factor for enhanced cartilage regeneration. By contrast, the platelet-derived growth factor-related proteins (PDGF R-beta and PDGF-AB), placental growth factor (PLGF), and vascular endothelial growth factor (VEGF-D) were more highly secreted by the cells cultured on the flat scaffold (H of FIG. 6). PDGF, a crucial growth factor for bone healing at the early stage, was recently found to regulate the proliferation of chondrocytes. VEGF is an effective angiogenic factor and has a role in controlling articular cartilage degeneration. Our findings revealed that whereas the cartilage regeneration-related growth factors were highly secreted by stem cells on the nanobridge scaffold, the crucial growth factors for cartilage degeneration were more highly secreted by the cells on the flat scaffold. Finally, the inventors analyzed the degree of chondrogenesis of stem cells on the nanobridge scaffold ex vivo. To this end, the transplanted scaffolds were separated from the rabbit cartilage, and the expression of collagen II by the stem cells was confirmed by immunofluorescence assay. Interestingly, the expression levels of the cartilage matrix and collagen II were higher in cells on the nanopatterned scaffold than those on the flat scaffold (J and K of FIG. 6), demonstrating that the nanobridge could promote the chondrogenesis of stem cells.

Our results have demonstrated that our rational design of a bioengineered stem cell nanopatterned scaffold as a transplantable nanobridge for cartilage restoration and regeneration was feasible and successful. In summary, our proposed flexible and biodegradable nanobridge scaffold containing a nanopatterned topography was used for the successful regeneration of defected cartilage tissue. Specifically, the nanobridge scaffold offers the following key benefits compared with the existing cell-based engineering techniques for cartilage regeneration: i) guidance of the host cells; ii) maintenance of the implanted cells and stem cells from the microfracture; 3) control of stem cell behavior; and 4) promotion of tissue reconstruction through optimization of the body's own resource (FIG. 7). The prepared nanobridge scaffold had a flexible and transplantable shape and was easily adaptable to cartilage tissue. It could bridge the divide between the host tissue and defected cartilage, promoting tissue regeneration with cartilage matrix formation (FIGS. 2 and 3). Both the flat and nanobridge scaffolds could prevent the loss of cells (FIGS. 5 and 6), allowing the secreted growth factors, ECM molecules, and proteins to be locked within the defected cartilage site (FIG. 6) covered with the scaffold. Additionally, the host cells and tissue were engaged by the guidance of the nanotopography of the scaffold surface, promoting the formation of an ECM similar to that of native cartilage tissue. The topographical guidance was a crucial factor for cartilage regeneration. On the basis of the nanotopography of the nanobridge scaffold, the morphological response, proliferation, and differentiation of the hMSCs could be controlled as well as the morphological response and migration of the chondrocytes (FIGS. 4 and 5).

Specifically, the nanotopography induced the hMSCs and chondrocytes to form a highly aligned cytoskeletal shape with enhanced elongation. With the hMSCs, it sequentially resulted in increased chondrogenesis, matrix formation, and secretion of the cartilage regeneration-related growth factors. As a result of the nanotopographical cues, the migration of host cells and their integration near the defected sites were promoted. Although more cells were maintained on the flat scaffold than on the nanopatterned scaffold, the ability of the nanobridge to contain the cells was confirmed, resulting in their highly increased expression of ECM-related markers. Compared with the flat scaffold, the transplantable nanobridge loaded with hMSCs offered better promotion of cartilage regeneration.

A sequence listing electronically submitted with the present application on Sep. 20, 2021 as an ASCII text file named 20210920_LC0432113_TU_SEQ, created on Sep. 20, 2021 and having a size of 1,000 bytes, is incorporated herein by reference in its entirety.

What is claimed is:

1. A scaffold comprising:
   a film having a plurality of linear nano-patterns formed and aligned in one direction on a surface of the film, the film having the plurality of nano-patterns prepared by a process comprising preparing a film having a surface on which the plurality of linear nano-patterns do not exist and forming the plurality of linear nano-patterns on the surface of the film; and
   stem cells adhered to the plurality of linear nano-patterns, wherein the plurality of linear nano-patterns include a ridge and a groove having each independently a width of 100 to 1,000 nm,
   wherein the plurality of linear nano-patterns have a height of 100 to 1000 nm.

2. The scaffold according to claim 1, wherein the plurality of linear nano-patterns include a ridge and a groove having each independently a width of 700 to 1000 nm.

3. The scaffold according to claim 1, wherein the plurality of linear nano-patterns have a height of 700 to 1000 nm.

4. The scaffold according to claim 1, wherein the stem cells are mesenchymal stem cells derived from human adipose tissues.

5. The scaffold according to claim 1, wherein the plurality of linear nano-patterns are formed of a material selected from the group consisting of polyurethane acrylate (PUA) resin, polyvinyl alcohol resin, polyethylene resin, polypropylene resin, polyethyleneglycol resin, poly(L-lactid-co-glycolide) resin, polycaprolactone (PCL) resin, polylactic acid (PLA) resin, polyglycolic acid (PGA) resin, chitosan, gelatin, collagen, and a combination thereof.

6. The scaffold according to claim 1, wherein the plurality of linear nano-patterns are formed of a material selected from the group consisting of polyurethane acrylate (PUA) resin, polyvinyl alcohol resin, polyethylene resin, polypropylene resin, polyethyleneglycol resin, poly(L-lactid-co-glycolide) resin, polycaprolactone (PCL) resin, polylactic acid (PLA) resin, polyglycolic acid (PGA) resin, chitosan, gelatin, and a combination thereof.

7. A method for treatment of a cartilage defect, the method comprising:
   adhering a surface of a scaffold to a cartilage defect site of a subject,
   wherein the scaffold comprises:
   a film having a plurality of linear nano-patterns formed and aligned in one direction on a surface of the film, the film having the plurality of nano-patterns prepared by a process comprising preparing a film having a surface on which the plurality of linear nano-patterns do not exist and forming the plurality of linear nano-patterns on the surface of the film; and
   stem cells adhered to the plurality of linear nano-patterns, wherein the plurality of linear nano-patterns include a ridge and a groove having each independently a width of 100 to 1000 nm,
   wherein the plurality of linear nano-patterns have a height of 100 to 1000 nm.

8. The method according to claim 7, wherein the plurality of linear nano-patterns include a ridge and a groove having each independently a width of 700 to 1000 nm.

9. The method according to claim 7, wherein the plurality of linear nano-patterns have a height of 700 to 1000 nm.

10. The method according to claim 7, wherein the stem cells are mesenchymal stem cells derived from human adipose tissues.

11. The method according to claim 7, further comprising:
    microfracturing a bone exposed on the cartilage defect site, wherein the scaffold is adhered to the microfractured site.

12. The method of claim 7, wherein the plurality of linear nano-patterns are formed of a material selected from the group consisting of polyurethane acrylate (PUA) resin, polyvinyl alcohol resin, polyethylene resin, polypropylene resin, polyethyleneglycol resin, poly(L-lactid-co-glycolide) resin, polycaprolactone (PCL) resin, polylactic acid (PLA)

resin, polyglycolic acid (PGA) resin, chitosan, gelatin, collagen, and a combination thereof.

13. The method of claim 7, wherein the plurality of linear nano-patterns are formed of a material selected from the group consisting of polyurethane acrylate (PUA) resin, polyvinyl alcohol resin, polyethylene resin, polypropylene resin, polyethyleneglycol resin, poly(L-lactid-co-glycolide) resin, polycaprolactone (PCL) resin, polylactic acid (PLA) resin, polyglycolic acid (PGA) resin, chitosan, gelatin, and a combination thereof.

14. The method of claim 7, further comprising:
before the adhering, perforating a hole in a bone exposed due to the cartilage defect.

15. A scaffold comprising:
a film having a plurality of ridges linearly aligned in one diction and a plurality of grooves each aligned in the one direction between neighboring ridges of the plurality of ridges on a surface of the film, the film having the plurality of ridges and the plurality of grooves prepared by a process comprising preparing a film having a surface on which the plurality of linear nano-patterns do not exist and forming the plurality of linear nano-patterns on the surface of the film; and
stem cells adhered to the film,
wherein the plurality of linear nano-patterns include a ridge and a groove having each independently a width of 100 to 1000 nm, and
wherein the plurality of linear nano-patterns have a height of 100 to 1000 nm.

16. The scaffold of claim 15, wherein the plurality of ridges and the plurality of grooves each have each independently a width of 700 to 1000 nm; and
the film has a height of 700 to 1000 nm.

* * * * *